United States Patent
Ramadoss et al.

(12)

(10) Patent No.: US 6,214,814 B1
(45) Date of Patent: Apr. 10, 2001

(54) USE OF BETULINIC ACID DERIVATIVES FOR INHIBITING CANCER GROWTH

(75) Inventors: Sunder Ramadoss, Delhi; Manu Jaggi, Haryana; Mohammad Jamshed Ahmed Siddiqui, Ghaziabad; Achla B. Khanna, Delhi, all of (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 09/251,309

(22) Filed: Feb. 17, 1999

Related U.S. Application Data

(63) Continuation-in-part of application No. 09/040,856, filed on Mar. 18, 1998, now Pat. No. 6,048,847.

(30) Foreign Application Priority Data

Nov. 18, 1998 (IN) .................................................. 3458/98

(51) Int. Cl.$^7$ .............................. A61K 31/56; C07J 53/00
(52) U.S. Cl. ........................................... 514/169; 552/510
(58) Field of Search ............................... 552/510; 514/169

(56) References Cited

U.S. PATENT DOCUMENTS 5,869,535 * 2/1999 Pezzuto et al. ..................... 514/640

FOREIGN PATENT DOCUMENTS 9426695 11/1994 (WO).
9629068 9/1996 (WO).

OTHER PUBLICATIONS

Fujioka, et al, Journal of Natural Products, vol. 57, No. 2, Feb. 1, 1994, pp. 243–247.

Hashimoto, et al, Bioorg. Med., Chem., vol. 5, No. 12, 1997, pp. 2133–2143.

Konoshima T. et al., Journal of Natural Products, vol. 50, No. 6, Nov. 1, 1987, pp. 1167–1170.

Miles, D. H., et al., Journal of Pharmaceutical Sciences, vol. 63, No. 4, Apr. 1, 1974, pp. 613–615.

J.S. Lee, et al., Chemical Abstracts+Indexes, vol. 125 No. 19, Nov. 4, 1996, p. 58.

Bishay, D.W. et al., Bulletion of Pharmaceutical Sciences, vol. 10, Part 2, Jan. 1, 1987, pp. 1–20.

Toda, A. et al, Chemical Abstracts, vol. 127, No. 2, Abstract 023542, Jul. 14, 1997.

Pradhan, B. P., et al, Indian J. Chem., Sect. B., vol. 32B, No. 11, pp. 1178–1180, 1993.

Patra, A. et al, Chemical Abstracts, vol. 111, No. 9, Abstract 078441, Aug. 28, 1989.

Protiva, J. et al, Collection of Czechoslovak Chemical Communications, vol. 42, No. 4, 1977, pp. 1220–1228.

Protiva, J. et al, Collection of Czechoslovak Chemical Communications, vol. 41, No. 4, 1976, pp. 1200–1207.

Protiva, J. et al, Collection of Czechoslovak Chemical Communications, vol. 46, No. 11, 1981, pp. 2734–2741.

Akira Inada, et al., Chemical and Pharmaceutical Bulletin, vol. 41, No. 3, Mar. 1, 1993, pp. 617–619.

Y. Noda, et al., Chemical and Pharmaceutical Bulletin, vol. 45, No. 10, Jan. 1, 1997, pp. 1665–1670.

Kim, D S H L, et al., Bioorganic & Medical Chemistry Letters, vol. 8, No. 13, Jul. 7, 1998, pp. 1707–1712.

Fujioka et al., Journal of Natural Products, vol. 57(2), 1994, pp. 243–247, 1994.*

Hashimoto et al., Bioorg. Med. Chem., vol. 5(12), 1997, pp. 2133–2143, 1994.*

Fujioka et al., Journal of Natural Products, vol. 57(2), pp. 243–247, 1994.*

Hashimoto et al, Bioorg. Med. Chem., vol. 5(12), pp. 2133–2143, 1997.*

Konoshima et al., Journal of Natural Products, vol. 50(6), pp. 1167–1170, 1987.*

* cited by examiner

*Primary Examiner*—Barbara P. Badio
(74) *Attorney, Agent, or Firm*—Ladas & Parry

(57) ABSTRACT

The invention relates to the use of betulinic acid and its derivatives for the inhibition and/or prevention or cancer growth. The invention also relates to novel betulinic acid derivatives useful for the inhibition of tumor/cancer cells and a process for the preparation of the derivatives. The invention also relates to the antileukemic, and antilymphoma activity of the betulinic acid derivatives, and the use of the derivatives for the treatment of prostate, ovarian and lung cancer.

6 Claims, 3 Drawing Sheets

USE OF BETULINIC ACID DERIVATIVES FOR INHIBITING CANCER GROWTH

This application is a continuation-in-part application of U.S. patent application Ser. No. 09/040,856, filed Mar. 18, 1998, now U.S. Pat. No. 6,048,847.

FIELD OF THE INVENTION

The invention relates to the use of betulinic acid and its derivatives for the inhibition and/or prevention or cancer growth. The invention also relates to novel betulinic acid derivatives useful for the inhibition of tumor/cancer cells and a process for the preparation of the derivatives. The invention also relates to the antileukemic, and anti-lymphoma activity of the betulinic acid derivatives, and the use of the derivatives for the treatment of prostate, ovarian and lung cancer.

BACKGROUND AND PRIOR ART REFERENCES TO THE INVENTION

Under the auspices of a National Cooperative Natural Product Drug Discovery Group supported by the National Cancer Institute, the potential antitumor activity of approximately 2500 extracts derived from globally collected plants was evaluated in a panel of enzyme based assays and in a battery of cultured human tumor cell lines. One such extract, prepared from the stem bark of Ziziphus mauritiana Lam. (Rhamnaceae), displayed selective cytotoxicity against cultured human melanoma cells (Nature Medicine, Vo. 1 (10), 1995, WO 96/29068). As a result of bioactivity guided fractionation, betulinic acid, a pentacyclic triterpene, was identified as a melanoma-specific cytotoxic agent. In follow-up studies conducted with a thymic mice carrying human melanomas, tumor growth was completely inhibited without toxicity. As judged by a variety of cellular responses, anti-tumor activity was mediated by the induction of apoptosis.

A number of triterpenoids, including betulinic acid, have several known medical applications, including use as anti-cancer drugs. Anderson et al., in WO 95/04526, have discussed the derivatives of triterpenoids which have been used in cancer therapy, including their activity against polyamines which are required by cells to grow at an optimal rate. Some of these triterpenoids have been found to interfere with enzymatic synthesis of polyamines required for optimal cell growth, and thus inhibit the growth of cancer cells, particularly by inhibiting ornithine decarboxylase (Yasukawa, K. et al., Oncology 48: 72–76, 1991), The anti-cancer activity of betulinic acid and some derivatives has been demonstrated using mouse sarcoma 180 cells implanted subcutaneously in nude mice (JP 87,301,580). Choi et al have shown that betulinic acid 3-monoacetate, and betulinic acid methyl ester exhibit $ED_{50}$ values of 10.5 and 6.8 µg/ml, respectively, against p388 lymphocytic leukemia cells (Choi, Y-H et al., Planta Medical vol. XLVII, pages 511–513, 1988).

Derivatives having $ED_{50}$ values greater than 4.0 µg/ml are considered not to have any significant anticancer activity. Table 1 indicates anticancer activity ($ED_{50}$ values) of a number of betulinic acid derivatives.

SUMMARY OF THE INVENTION

The present invention provides betulinic acid derivatives, compositions comprising betulinic acid derivatives, use of the betulinic acid derivatives for killing or inhibiting multiplication of cancer cells, a process for the synthesis of the derivatives of betulinic acid and testing the bio-activity of the derivatives using cultured human leukemia (MOLT-4, Jurkat E6.1, HL60, CEM.CM3), lymphoma cells (BRISTOL-8, U937), prostate cancer cells (DU 145), lung cancer cells (A 549) and ovarian cancer cells (PA-1) as the monitor.

In a preferred embodiment, a pharmaceutically acceptable carrier, diluent, or solvent is used. The invention also provides a method of treatment for humans, mammals, or other animals suffering from cancer or other tumors. The method may suitably comprise administering a therapeutically effective dose of the derivative in a pharmaceutical composition so as to kill or inhibit the multiplication of cancer or tumor cells. The method of treatment of the present invention is particularly useful in the treatment of leukemias and lymphomas, and in general in the treatment of prostate, ovarian and lung cancer.

OBJECTS OF THE INVENTION

An object of the present invention is to provide a method and composition for inhibiting tumor growth and, particularly, for inhibiting the growth of leukemias and lymphomas and for inhibiting the growth of prostate, ovarian and lung cancer using betulinic acid, one or more betulinic acid derivatives or a combination thereof.

A further object of the invention is to provide a treatment method using at least one betulinic acid derivative to prevent the growth of cancerous cells, preferably the betulinic acid derivative is administered systematically.

A still further object of the invention is to provide betulinic acid derivatives and a process for producing such derivatives.

Yet another object of the invention is to provide pharmaceutical formulations containing betulinic acid derivatives alone or in combination.

Still another object of the invention is to overcome the problem of high toxicity associated with standard chemo-therapeutic agents by using a natural product-derived compound, e.g., betulinic acid derivatives.

Yet another object of the invention is to overcome the problem of insufficient availability associated with synthetic anticancer agents by using synthetic derivatives of betulinic acid.

BRIEF DESCRIPTION OF THE ACCOMPANYING DRAWINGS

DETAILED DESCRIPTION OF THE INVENTION

Figure 1:
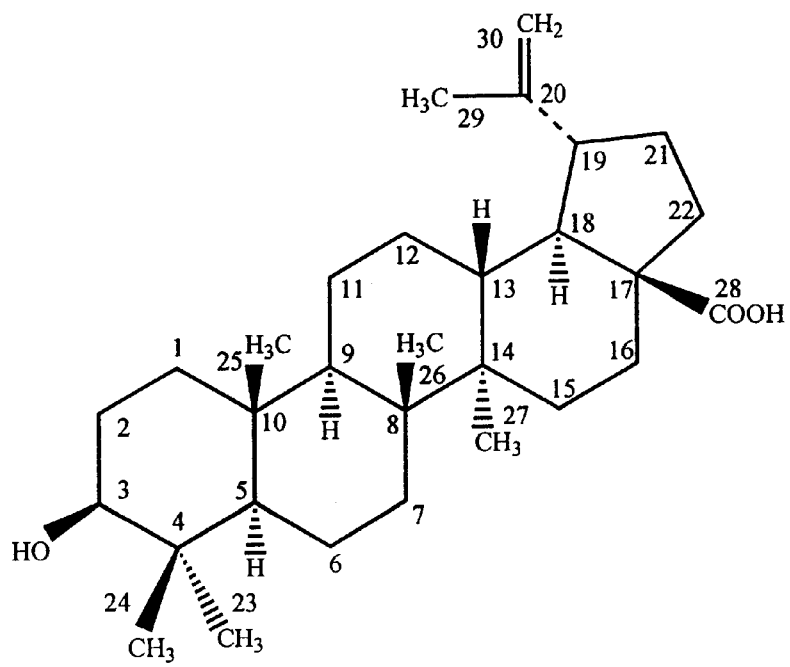
FIG. 1 represents the formula for betulinic acid.

The invention mainly relates to a method of treating a patient with leukemia or lymphoma or prostate, lung or ovarian cancer, said method comprising administering a pharmaceutically effective amount of betulinic acid, or a betulinic acid derivative alone or in combination, concurrently or in a mixture to a patient. A patient may be a human, mammal or other animal. The $ED_{50}$ value of active betulinic acid derivatives against leukemia or lymphoma preferably is in the range of 0.4 to 3.5 μg/ml. The preferred $ED_{50}$ values of active betulinic acid derivatives are in the ranges of 0.4 to 4.0 μg/ml, 0.7 to 4.0 μg/ml, 1.2 to 4.0 μg/ml against prostate cancer, lung cancer and ovarian cancer respectively.

The invention also relates to novel derivatives of betulinic acid, which are used for treating a patient with leukemia or lymphoma or prostate, lung or ovarian cancer. The general formula of betulinic acid is shown as structure 1 herebelow:

STRUCTURE 1

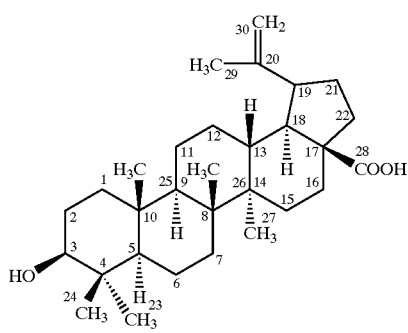

The novel derivatives of betulinic acid are shown in structures 2 to 6 herebelow.

STRUCTURE 2

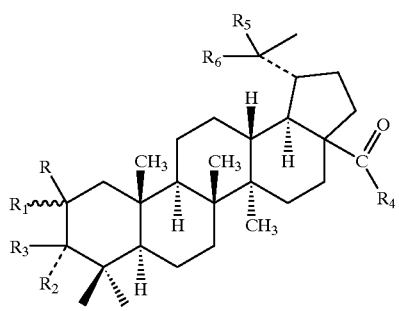

where R, $R_1$, $R_2$, $R_3$, $R_4$, $R_5$ and $R_6$ independently or in combination represent:

R is H;

$R_1$ is H, Br, Cl, F or I;

$R_2$ is H and $R_3$ is OH, $OCOCH_3$, $OCO(CH_2)_nCH_3$ (where n=1 to 5), $OCO(CH_2)_mCH_3$ (where m=1 to 5), $OCOC_6H_5$, $OSO_2CH_3$, $NH_2$, $NHCH_2CH_2OH$, $NHCH_2CH_2OCOCH_3$, $N=CHC_6H_3(NO_2)_2$, $N=CHC_6H_4Cl$, $N=CHC_6H_4Br$, $N=CHC_6H_4NO_2$, $N=CHC_6H_3Br_2$, $N=CHC_6H_3Cl_2$, $N=CHC_6H_3(CH_3)CF_3$, $N=CHC_6H_4CF_3$, $N=CHC_6H_4F$, $OCOC_6H_2Cl_3$, $OCOCH(OCOCH_3)CH_3$, $OCOCH(OCOCH_3)C_6H_5$, $OCOCH_2C_6H_5$, $OCO(CHOH)CH_3$; $OCOC_6H_4Br$, $OCOC_6H_4Cl$, $OCOC_6H_4F$, $OCOC_6H_4I$, $OCOC_6H_3Cl_2$, $OCOC_6H_3F_2$, or $OCOC_6H_4CF_3$ or $R_2$ and $R_3$ together are O, $NNHC_6H_5$, $NNHC_6H_2Cl_3$, $NNHC_6H_4F$, $NNHC_6H_4OCH_3$, $NNHC_6H_4OH$, $NNHC_6H_3(Br)(OCH_3)$ or N—OX (X being H, $COCH_3$, $SO_2C_6H_4CH_3$ or $CO(CH_2)_pCH_3$ (where p=1 to 5), $R_4$ is OH, —$OCH_3$, $O(CH_2)_qCOOCH_3$, $O(CH_2)_qCOOC_2H_5$, $O(CH_2)_q$, COOH, $O(CH_2)_qCOCl$ (where q=1 to 5), $OCH_2CH_2OC_2H_5$, $OCH_2CH_2OH$, $OCH_2CH_2OCOCH_3$, Cl, $N_3$, $NHNH_2$, $C_6H_4OMe$, $HNNHC_6H_2Cl_3$, $NH_2$, or $NH(CH_2)_rCH_3$ (where r=0 to 9);

$R_5$ is H, or Br;

$R_6$ is $CH_3$, $CH_2Br$, $CH_2OH$, CHO, $CH_2OCOCH_3$, COOH, $COO(CH_2)_tCOOCH_3$, $COO(CH_2)_tC_2H_5$, $COO(CH_2)_tCOOH$ (where t=1 to 5); or $R_5$ and $R_6$ together are >C=$CH_2$ or >CH—$CH_3$.

STRUCTURE 3

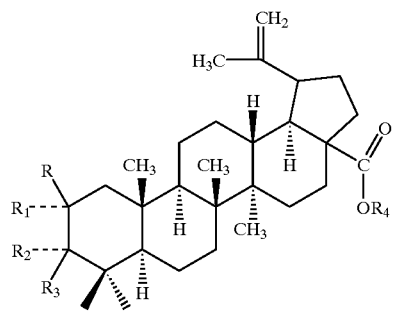

wherein

R=H;

$R_1$=H;

$R_2$=H;

$R_3$=$OSO_2CH_3$, $NHCH_2CH_2OH$, $N=CHC_6H_4F$, $N=CHC_6H_4Cl$, $N=CHC_6H_4NO_2$, $OCOC_6H_4Br$, $OCOC_6H_3F_2$, $OCOC_6H_4CF_3$, or $OCOC_6H_4F$ and $R_4$=H or $CH_2COOCH_3$

STRUCTURE 4

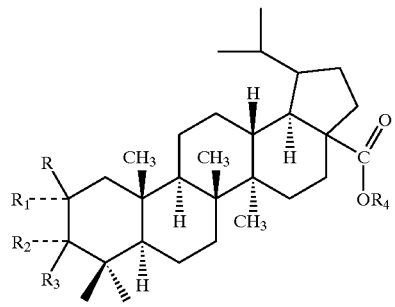

wherein

R=H;

$R_1$=H;

$R_2$=H;

$R_3$=$NH_2$, $OSO_2CH_3$, $NHCH_2CH_2OH$, $N=CHC_6H_4NO_2$, $N=CHC_6H_4F$, $N=CHC_6H_4Br$, $OCOC_6H_4Br$, $NHNHC_6H_5$, $NHNHC_6H_4OMe$, $OCOC_6H_3F_2$, $OCOC_6H_4CF_3$, $OCOC_6H_4F$, $N=CHC_6H_4Cl$, $N=CHC_6H_3F_2$, or $NHCH_2CH_2OCOCH_3$ and
$R_4=H$.

STRUCTURE 5

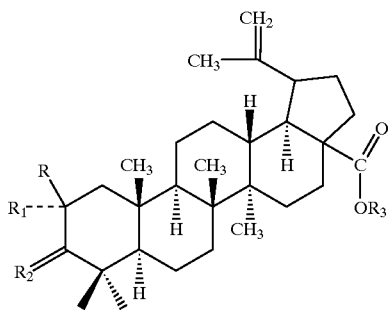

wherein
$R=H$;
$R_1=H$;
$R_2=NNHC_6H_4F$, or $NNHCH(OH)C_6H_5$ and
$R_3=H$.

STRUCTURE 6

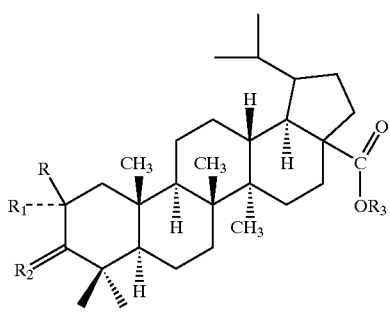

wherein
$R=H$;
$R_1=H$ or $Br$;
$R_2=NNHCOC_6H_5$, $NOCH_2C_6H_5$, $NNHCH_2C_6H_5$, $NNHC_6H_4F$, or
O and $R_3=H$ or $COOCH_2CH_2COOCH_3$.

The invention also relates to methods of preparing the betulinic acid derivatives. In the Examples below the term "substrate" refers to either betulinic acid, dihydrobetulinic acid or their derivatives as starting material unless otherwise indicated. Dihydrobetulinic acid is obtained from betulinic acid by reduction of $C_{20}$-$C_{29}$ double bond, whereas dihydrobetulinic acid derivatives refers to its derivatisation at either $C_3$ and/or $C_{17}$ positions.

Conventional procedures known to those skilled in the art can be used in the preparation of the various betulinic acid derivatives wherein the starting material is betulinic acid or a derivative thereof unless otherwise specifically mentioned.

Systemic administration refers to oral, rectal, nasal, transdermal and parental (i.e., intramuscular, intraperitoneal, subcutaneous or intravenous). In accordance with good clinical practice, it is preferred to administer the composition at a dose that will produce antiangiogenic effects without causing undue harmful side effects. The composition may be administered either alone or as a mixture with other therapeutic agents. The composition of the invention may contain one or more derivatives of betulinic acid or betulinic acid in combination with one or more derivatives of betulinic acid.

The compositions of this invention may contain physiologically acceptable diluents, fillers, lubricants, excipients, solvents, binders, stabilizers, and the like. Diluents that may be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that may be used in the compositions include but are not limited to starch, gelatin and fillers such as sucrose, glucose, dextrose and lactose.

Natural and synthetic gums that may be used in the compositions include but are not limited to sodium alginate, ghatti gum, carboxymethyl cellulose, methyl cellulose, polyvinyl pyrrolidone and veegum. Excipients that may be used in the compositions include but are not limited to microcrystalline cellulose, calcium sulfate, dicalcium phosphate, starch, magnesium stearate, lactose, and sucrose. Stabilizers that may be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that may be used include but are not limited to Ringers solution, water, distilled water, dimethyl sulfoxide to 50% in water, propylene glycol (neat or in water), phosphate buffered saline, balanced salt solution, glycol and other conventional fluids.

Compositions which provide from about 10 mg to 1000 mg of the composition per unit dose are preferred. The compositions may be in the form of tablets, lozenges, capsules, powders, aqueous or oily suspensions, syrups, elixirs, implants or aqueous solutions and the like which are prepared by any conventional method. The nature of the composition used will, of course, depend on the desired route of administration. The human dosage of the compounds is in the range of 1.0 to 200 mg/kg/day and the preferred range is 1.0 to 50 mg/kg/day.

The procedures described below are either used alone or in combination to produce the derivatives.

PREPARATION OF BETULINIC ACID DERIVATIVES

EXAMPLE 1

Preparation of 3-O-Benzoyl Derivatives

Substrate in organic base is treated with suitable benzoyl chloride for approximately 6–16 hours at an ambient temperature. Examples of benzoyl chloride that can be used are represented by general formula $R_n(Ar)CoCl$ wherein n=1 to 3, R=H, Cl, Br, F, or $CF_3$ and Ar=$C_6H_5$, $C_6H_4$, $C_6H_3$ or $C_6H_2$. The reaction was worked up by addition of water and extraction with organic solvent. The organic layer was dried over anhydrous sodium sulphate, evaporated and residue crystallized to yield pure 3-o-benzoyl derivatives respectively. Examples of organic bases that can be used are pyridine and piperidine.

EXAMPLE 2

Preparation of 3-O-Mesylate Derivatives

Substrate is dissolved in halogenated solvent and methane sulphonyl chloride is added slowly at 5–10° C. The mixture is stirred at an ambient temperature for 2–4 hours. The reaction mixture is worked up by washing the organic layer with water. The organic layer is dried over anhydrous sulfate, filtered, evaporated to dryness to obtain a residue which was crystallized from acetonitrile to yield pure 3-o-mesylate derivative.

EXAMPLE 3

Preparation of 3-Phenyl Hydrazino or its Phenyl Substituted Derivative 3-phenylhydrazone or its phenyl substituted derivative of betulinic acid or dihydrobetulinic acid is dissolved in glacial acetic acid and shaken under hydrogen atmosphere (50–70-psi) in the presence of platinum sponge catalyst for 3–5 hours. The reaction mixture was filtered, the mother liquor was evaporated under vacuum to remove glacial acetic acid and the residue crystallized from alcoholic solvent to yield pure 3-phenyl hydrazino or its phenyl substituted derivative. Alcoholic solvents used are methanol, ethanol or isopropanol.

EXAMPLE 4

Preparation of 3-N-Hydroxyethyl Derivatives 3-oxo-derivative is dissolved in absolute alcoholic solvent such as methanol, and/or ethanol and 15–20% alcoholic hydrochloric acid and 2-aminoethanol is added. The reaction mixture is stirred at room temperature for 30–60 minutes. To this sodium cyanoborohydride is added and stirring is continued at room temperature for approximately 72 hours. The mixture is worked up by adding water followed by filtration of solid to yield crude product, which was crystallized from alcohol to yield pure 3-N-hydroxyethyl derivative.

EXAMPLE 5

Preparation of 3-N-Benzylidene Derivative

3-Amino derivative is dissolved in alcoholic solvent, such as methanol and/or ethanol. Benzaldehyde or substituted benzaldehyde derivative is added in the presence or absence of alkali carbonate, such as sodium or potassium carbonate. The mixture was stirred for a few hours at ambient temperature to approximately 50° C. The reaction mixture was worked up by removing alcohol under vacuum, and water was added. The aqueous layer is either filtered or extracted with halogenated organic solvent, followed by evaporation to yield 3-N-benzylidene derivative.

EXAMPLE 6

Preparation of 3-Amino Derivatives 3-amino derivative is dissolved in glacial acetic acid and shaken under hydrogen atmosphere (60–70 psi) in the presence of platinum oxide catalyst for several hours. The reaction mixture is filtered, molten liquor is evaporated under vacuum to remove glacial acetic acid and the residue worked up in the usual manner to yield the corresponding 3-amino derivative.

EXAMPLE 7

Preparation of 3-Oxo Derivatives

The substrate was dissolved in the organic solvent and a conventional oxidizing agent was added under normal reaction conditions. The reaction was worked up to yield the corresponding 3-oxo derivatives in pure form.

EXAMPLE 8

Preparation of 3-Oximino Derivatives

The 3-oxo derivative was dissolved in an alcoholic solvent. To this was added hydroxylamine hydrochloride and sodium acetate and the mixture was refluxed for a few hours. The reaction mixture was evaporated to dryness. The reaction was worked up as described in Method 1 to yield crude-3-oximino derivatives which was crystallized to yield the corresponding pure 3-oximino derivative.

EXAMPLE 9

Preparation of Phenylhydrazone of 3-Oxo Derivative

Phenylhydrazine was added to 3-oxo derivative dissolved in alcoholic solvent and refluxed for four hours. The reaction was worked up as described in Method 1 to yield the corresponding phenyl hydrazone derivative in the pure form.

EXAMPLE 10

In vitro cytotoxic activity of betulinic acid derivatives was determined by performing the MTT cytotoxicity assay (Mosmann T., J Immunological Methods, 65: 55; 1983). Briefly, the cultured tumor cells were separately seeded in a 96-well culture plate and co-incubated with betulinic acid or its derivatives dissolved in methanol, dimethylformamide, dimethyl sulfoxide or isopropyl alcohol with relevant controls at 37° C. in a $CO_2$ incubator. After 72 hours, the assay was terminated and percent cyotoxicities calculated. As shown in Table 1, metabolic activity of leukemia cells (MOLT-4, Jurkat E6.1, CEM.CM3) was inhibited by active betulinic acid derivatives, i.e., an $ED_{50}$ value of about 0.4–3.5 µg/ml. The $ED_{50}$ value of active betulinic acid derivatives for lymphoma cells (BRISTOL-8, U937) was in the range of 1.8 to 3.1 µg/ml. Further active betulinic acid derivatives showed an $ED_{50}$ value of 0.4–4.0 µg/ml, 1.2–4.0 µg/ml and 0.7–4.0 µg/ml against DU145 (human prostate), PA-1 (human ovary) and A549 (human lung) respectively.

TABLE 1

| | | Cell line | | | | | | | |
| --- | --- | --- | --- | --- | --- | --- | --- | --- | --- |
| S. No | Derivative | MOLT-4 | CEM.CM3 | JurkatE6.1 | BRISTOL 8 | U937 | DU145 | PA-1 | A549 |
| 1 | Betulinic acid | 1.23 | 0.98 | 0.65 | 0.84 | 0.69 | 1.13 | >10 | >10 |
| 2 | MJ751-RS | 0.7 | >4.0 | >4.0 | >4.0 | >4.0 | >4.0 | 1.7 | >4.0 |
| 3 | MJ813-RS | 1.8 | >4.0 | 3.5 | 3.0 | >4.0 | 2.9 | 2.9 | >4.0 |

TABLE 1-continued

| S. No | Derivative | MOLT-4 | CEM.CM3 | JurkatE6.1 | BRISTOL 8 | U937 | DU145 | PA-1 | A549 |
|---|---|---|---|---|---|---|---|---|---|
| 4 | MJ927-RS | 1.7 | >4.0 | 2.8 | 2.7 | >4.0 | 4.0 | 1.2 | 1.2 |
| 5 | MJ939-RS | 1.4 | 2.6 | >4.0 | 3.1 | 2.9 | 1.4 | 1.6 | 4.0 |
| 6 | MJ940-RS | 0.4 | 3.1 | 3.8 | 1.9 | >4.0 | 0.4 | 1.6 | 4.0 |
| 7 | MJ942-RS | 0.5 | 3.5 | >4.0 | 1.8 | >4.0 | 0.9 | 4.0 | 0.7 |
| 8 | MJ944-RS | >4.0 | 3.5 | >4.0 | 3.0 | >4.0 | >4.0 | 1.8 | >4.0 |

EXAMPLE 11

Figure 2:
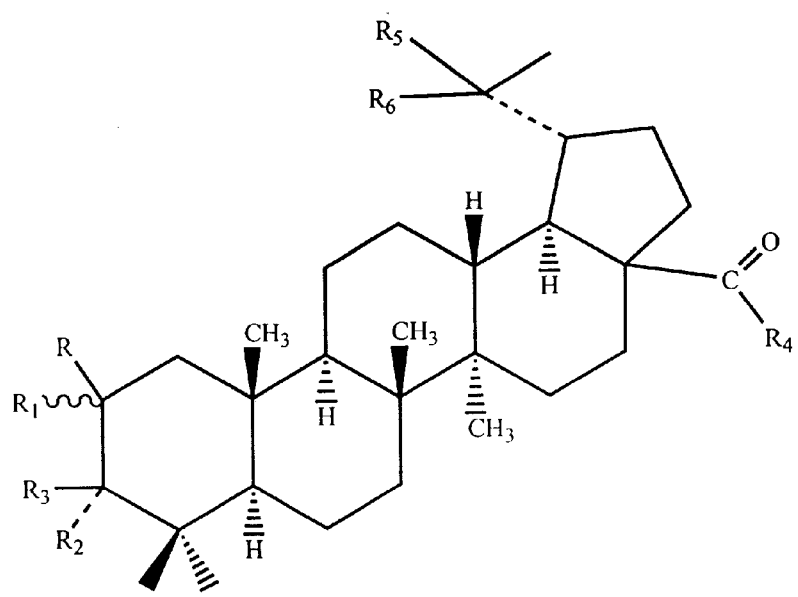
FIG. 2 represents a general formula of derivatives of betulinic acid.
Figure 3:
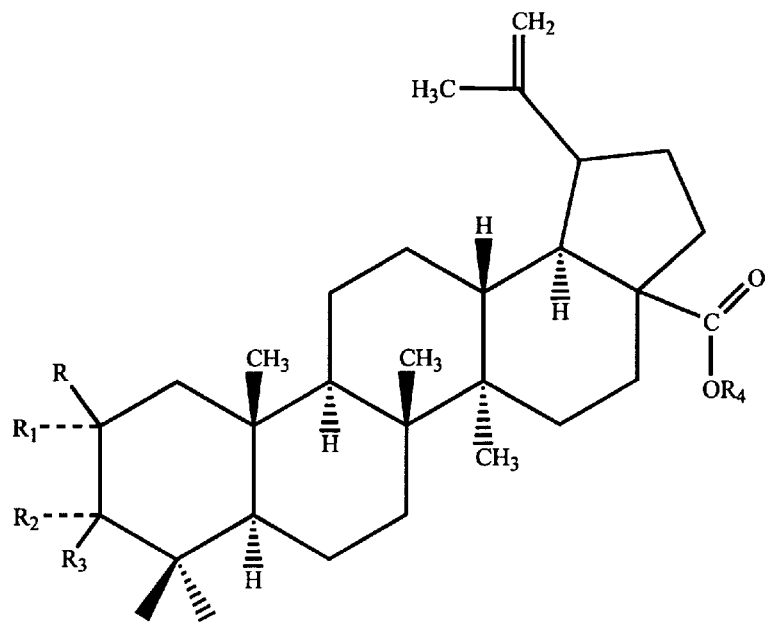
FIG. 3 represents a general formula of derivatives of betulinic acid.
Figure 4:
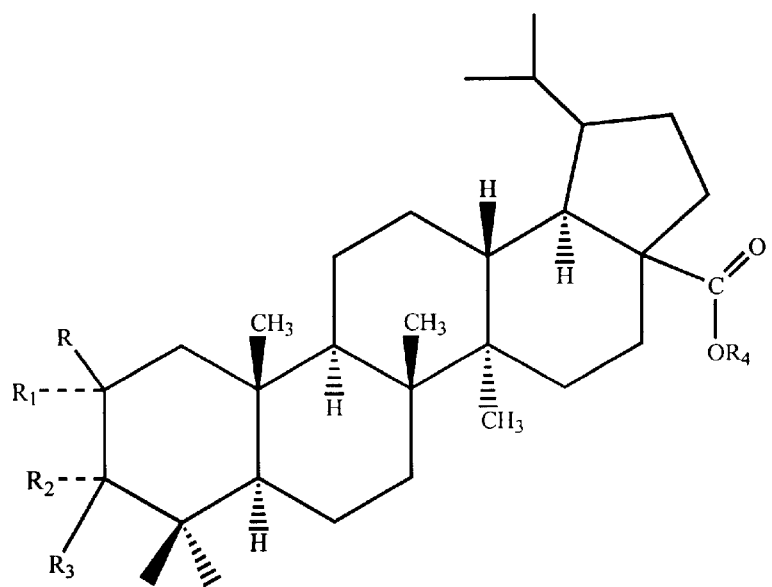
FIG. 4 represents a general formula of derivatives of betulinic acid.
Figure 5:
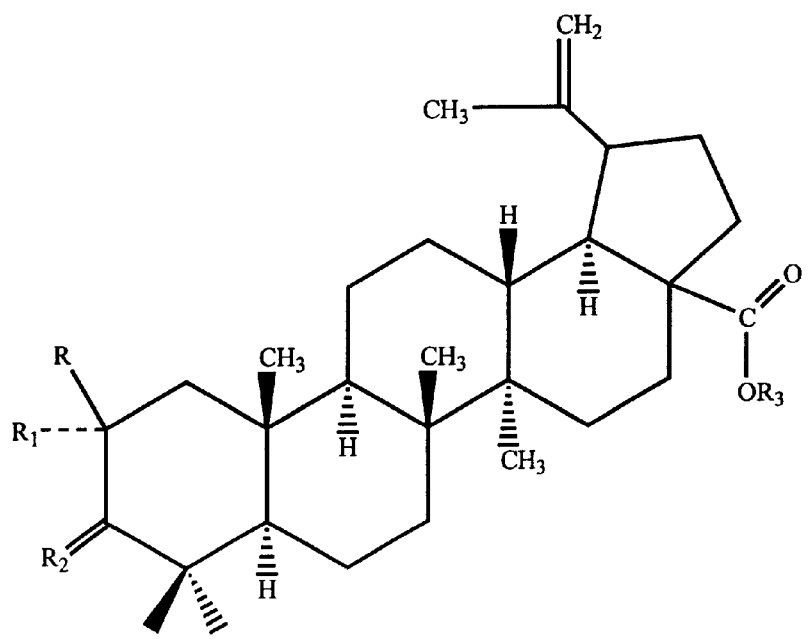
FIG. 5 represents a general formula of derivatives of betulinic acid.
Figure 6:
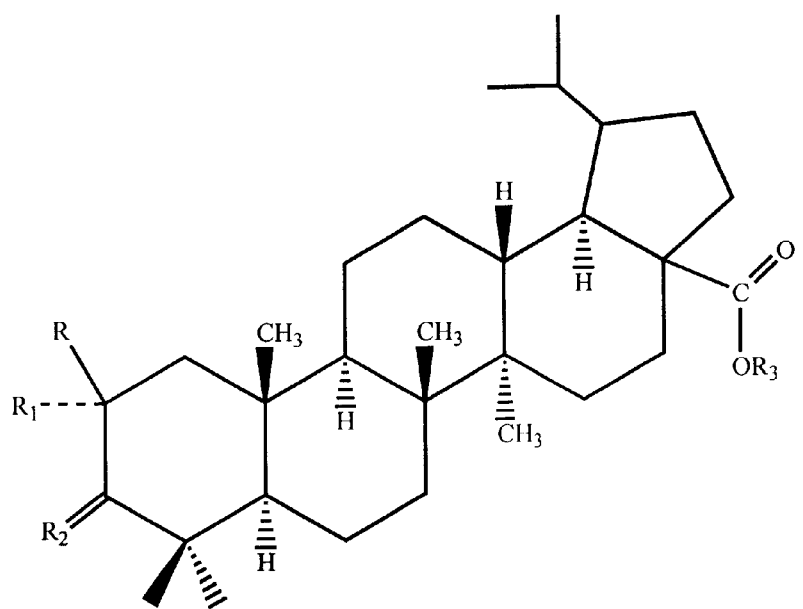
FIG. 6 represents a general formula of derivatives of betulinic acid.

Structural changes at the $C_2$, $C_3$ and/or $C_{17}$ positions of betulinic acid as shown in FIG. 2, were made and forty-four derivatives of betulinic acid were prepared. The derivatives were characterized on the basis of spectral data. Tables II to Table V include descriptions of the derivatives based on the basic skeleton of betulinic acid as shown in FIGS. 3 to 6 respectively, and include the structures of the eight derivatives listed in Table I.

TABLE II

| Code | R | $R_1$ | $R_2$ | $R_3$ | $R_4$ |
|---|---|---|---|---|---|
| MJ751RS | H | H | H | $OSO_2CH_3$ | H |
| MJ790RS | H | H | H | $NHCH_2CH_2OH$ | H |
| MJ812RS | H | H | H | $N=CHC_6H_4F(2)$ | H |
| MJ835RS | H | H | H | $N=CHC_6H_4Cl(3)$ | H |
| MJ839RS | H | H | H | $N=CHC_6H_4NO_2(2)$ | H |
| MJ843RS | H | H | H | $OCOC_6H_4Br(2)$ | H |
| MJ926RS | H | H | H | $OCOC_6H_3F_2(2,3)$ | H |
| MJ929RS | H | H | H | $OCOC_6H_3F_2(3,4)$ | H |
| MJ934RS | H | H | H | $OCOC_6H_3F_2(3,5)$ | H |
| MJ936RS | H | H | H | $OCOC_6H_3F_2(2,4)$ | H |
| MJ939RS | H | H | H | $OCOC_6H_4CF_3(3)$ | H |
| MJ942RS | H | H | H | $OCOC_6H_4CF_3(2)$ | H |
| MJ951RS | H | H | H | $OCOC_6H_4F(4)$ | H |
| MJ953RS | H | H | H | $OCOC_6H_3F_2(2,3)$ | $CH_2COOCH_3$ |

TABLE III

| Code | R | $R_1$ | $R_2$ | $R_3$ | $R_4$ |
|---|---|---|---|---|---|
| MJ692-RS | H | H | H | $NH_2$ | H |
| MJ789-RS | H | H | H | $OSO_2CH_3$ | H |
| MJ830-RS | H | H | H | $NHCH_2CH_2OH$ | H |
| MJ839-RS | H | H | H | $N=CHC_6H_4NO_2(2)$ | H |
| MJ840-RS | H | H | H | $N=CHC_6H_4F(2)$ | H |
| MJ841-RS | H | H | H | $N=CHC_6H_4NO_2(3)$ | H |
| MJ842-RS | H | H | H | $N=CHC_6H_4Br(4)$ | H |
| MJ846-RS | H | H | H | $OCOC_6H_4Br(2)$ | H |
| MJ909-RS | H | H | H | $NHNHC_6H_5$ | H |
| MJ912-RS | H | H | H | $NHNHC_6H_4OMe(4)$ | H |
| MJ927-RS | H | H | H | $OCOC_6H_3F_2(2,3)$ | H |
| MJ931-RS | H | H | H | $OCOC_6H_3F_2(3,4)$ | H |
| MJ937-RS | H | H | H | $OCOC_6H_3F_2(2,4)$ | H |
| MJ940-RS | H | H | H | $OCOC_6H_4CF_3(3)$ | H |
| MJ943-RS | H | H | H | $OCOC_6H_4CF_3(2)$ | H |
| MJ947-RS | H | H | H | $OCOC_6H_4F(2)$ | H |
| MJ952-RS | H | H | H | $OCOC_6H_4F(4)$ | H |
| MJ991-RS | H | H | H | $N=CHC_6H_4Cl(2)$ | H |
| MJ998-RS | H | H | H | $N=CHC_6H_3F_2(3,4)$ | H |
| MJ999-RS | H | H | H | $N=CHC_6H_3F_2(3,5)$ | H |
| MJ1001-RS | H | H | H | $NHCH_2CH_2OCOCH_3$ | H |

TABLE IV

| Code | R | $R_1$ | $R_2$ | $R_3$ |
|---|---|---|---|---|
| MJ826-RS | H | H | $NNHC_6H_4F(4)$ | H |
| MJ831-RS | H | H | $NNHCH(OH)C_6H_5$ | H |
| MJ921-RS | H | H | $NNHC_6H_4F(2)$ | H |

TABLE V

| Code | R | $R_1$ | $R_2$ | $R_3$ |
|---|---|---|---|---|
| MJ807-RS | H | H | $NNHCOC_6H_5$ | H |
| MJ813-RS | H | H | $N-OCH_2C_6H_5$ | H |
| MJ821-RS | H | H | $NNHCH_2C_6H_5$ | H |
| MJ874-RS | H | H | O | $COOCH_2CH_2COOCH_3$ |
| MJ829-RS | H | H | $NNHC_6H_4F(4)$ | H |
| MJ922-RS | H | H | $NNHC_6H_4F(2)$ | H |

Numerals in parentheses after the functional groups in the above tables indicate the position of substituents (e.g. $NO_2$, Cl, F or Br) on the benzene ring.

EXAMPLE 12

A suitable formulation of betulinic acid derivatives was prepared as follows. Betulinic acid derivatives were solubilized in a minimum volume of methanol. Betulinic acid derivatives may also be solubilized in isopropyl alcohol, dimethylformamide, dimethylsulfoxide or any other suitable solvent. Substituted beta-cyclodextrin, such as 2-hydroxypropyl beta-cyclodextrin, or sulfobutyl ether beta-cyclodextrin was separately dissolved in water to a concentration of approximately 50 to 1000 mg per ml, preferably 250 to 750 mg per ml. The solubilized betulinic acid or its derivative was added in small aliquots to the derivatized beta cyclodextrin solution and sonicated at low temperature until a clear solution developed. The organic solvent was then removed by rotary evaporation and the final solution filtered to give a sterile product. The resulting solution was lyophilized.

What is claimed is:

1. A betulinic acid derivative having structure 4:

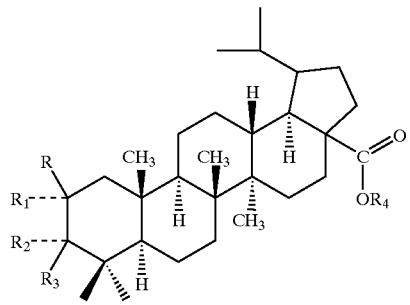

wherein

R=H;

R$_1$=H;

R$_2$=H;

R$_3$=OSO$_2$CH$_3$, NHCH$_2$CH$_2$OH, N=CHC$_6$H$_4$NO$_2$, N=CHC$_6$H$_4$F, N=CHC$_6$H$_4$Br, OCOC$_6$H$_4$Br, NHNHC$_6$H$_5$, NHNHC$_6$H$_4$OMe, OCOC$_6$H$_3$F$_2$, OCOC$_6$H$_4$CF$_3$, OCOC$_6$H$_4$F, N=CHC$_6$H$_4$Cl, N=CHC$_6$H$_3$F$_2$, or NHCH$_2$CH$_2$OCOCH$_3$ and

R$_4$=H.

2. A composition comprising a betulinic acid derivative of claim 1, and a pharmaceutically acceptable additive, diluent, excipient, solvent, binder, stabilizer, carrier, filer or lubricant.

3. The composition as claimed in claim 2, which provides 10 mg to 1000 mg per unit of the dose of betulinic acid derivative.

4. A betulinic acid derivative of the formula

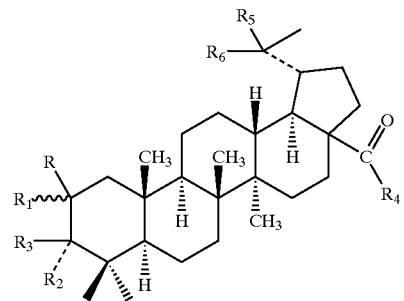

wherein R, R$_1$, R$_2$, R$_3$, R$_4$, R$_5$ and R$_6$ independently or in combination represent the following groups:

R is H;

R$_1$ is H, Br, Cl, F or I;

R$_2$ is H;

R$_3$ is NHCH$_2$CH$_2$OH, N=CHC$_6$H$_3$(NO$_2$)$_2$, OSO$_2$CH$_3$, N=CHC$_6$H$_4$Br, N=CHC$_6$H$_4$Cl, N=CHC$_6$H$_4$NO$_2$, NHCH$_2$CH$_2$OCOCH$_3$, N=CHC$_6$H$_3$(CH$_3$)CF$_3$, N=CHC$_6$H$_4$CF$_3$, N=CHC$_6$H$_3$Br$_2$, N=CHC$_6$H$_3$Cl$_2$, N=CHC$_6$H$_4$F, OCOC$_6$H$_3$Cl$_2$, OCOC$_6$H$_3$F$_2$, OCOC$_6$H$_2$Cl$_3$, or OCOC$_6$H$_4$CF$_3$;

R$_4$ is OH; and

R$_5$ and R$_6$ together with the carbon atom to which they are attached are >C=CH$_2$, or >CH—CH$_3$.

5. A composition comprising a betulinic acid derivative as claimed in claim 4 and a pharmaceutically acceptable additive, carrier, diluent, solvent, filler, lubricant, excipient, binder or stabilizer.

6. The composition as claimed in claim 5 in the form of a tablet, lozenge, capsule, powder, aqueous or oily suspension, syrup, elixir, implant or aqueous solution.

* * * * *